United States Patent [19]

Parnell

[11] Patent Number: 5,128,132
[45] Date of Patent: Jul. 7, 1992

[54] ERIODICTYON COMPOSITIONS AND METHODS FOR TREATING INTERNAL MUCOUS MEMBRANES

[75] Inventor: Francis W. Parnell, Ross, Calif.

[73] Assignee: Parnell Pharmaceuticals, Inc., San Rafael, Calif.

[21] Appl. No.: 608,336

[22] Filed: Nov. 2, 1990

Related U.S. Application Data

[63] Continuation-in-part of Ser. No. 499,952, Mar. 26, 1990, Pat. No. 5,015,474, which is a continuation-in-part of Ser. No. 275,124, Nov. 22, 1988, Pat. No. 4,938,963.

[51] Int. Cl.⁵ .................... A61K 35/78; A61K 31/00; A61K 47/00
[52] U.S. Cl. .................... 424/195.1; 424/9; 424/45; 514/783; 514/849
[58] Field of Search .................... 424/195.1, 9, 45; 514/849, 783

[56] References Cited

U.S. PATENT DOCUMENTS

| | | | |
|---|---|---|---|
| 164,674 | 6/1875 | Cooper | 424/195.1 |
| 174,442 | 3/1876 | Rohrer | 424/195.1 |
| 395,346 | 1/1889 | Poe | 424/195.1 |
| 404,422 | 6/1889 | Maxwell | 424/195.1 |
| 3,965,908 | 6/1976 | Posthuma et al. | |
| 4,128,863 | 12/1978 | Lundmark et al. | |
| 4,184,974 | 1/1980 | Van Leuven | |
| 4,205,073 | 5/1990 | Sherlock et al. | 424/266 |
| 4,232,003 | 11/1980 | Posthuma et al. | |
| 4,267,168 | 5/1981 | Van Leuven | |
| 4,347,237 | 8/1982 | Evenstad et al. | |
| 4,409,138 | 10/1983 | Maltz | |
| 4,438,100 | 3/1984 | Balslev et al. | |
| 4,559,322 | 12/1985 | Maltz | |
| 4,617,293 | 10/1986 | Wahlig et al. | |
| 4,661,475 | 4/1987 | Bayerlein et al. | 424/54 |
| 4,906,169 | 3/1990 | Chien et al. | 424/448 |
| 4,906,476 | 3/1990 | Radhakrishnan | 424/450 |
| 4,933,169 | 6/1990 | Shanbrom | |
| 4,938,963 | 7/1990 | Parnell | 424/440 |
| 4,939,169 | 7/1990 | Bundy et al. | |
| 4,966,171 | 9/1990 | Chang et al. | 424/449 |
| 4,983,378 | 1/1991 | Parnell | 424/48 |

FOREIGN PATENT DOCUMENTS 821525 8/1969 Canada .
0015544 9/1980 European Pat. Off. .

OTHER PUBLICATIONS

Steinmetz E. F. Codex Vegetabilis 1957 Amsterdam #432.
National Formulary 16th Ed. 1985 US Pharmacopeial Convention #1560.
Coon, *The Dictionary of Useful Plants*, pp. 20, 152 (1974).
Coon, *Using Plants for Healing*, p. 122 (1963).
Fox et al., *J. Am. Dental Assoc.*, vol. 110, pp. 519–525 (1985).
Grieve, *A Modern Herbal*, vol. II, p. 865 (1959).
Harris, *The Complete Herbal*, p. 197 (1972).
Huson, *Mastering Herbalism: A Practical Guide*, p. 32 (1974).
Hutchens, *Indian Herbalogy of North America*, pp. 317–318 (1975).
Lewis et al., *Medical Botany: Plants Affection Man's Health*, p. 301 (1977).
Moore, *Los Remedios de la Gente*, p. 17 (1977).
Spoerke, *Herbal Medications*, pp. 183, 185–186 (1980).
Trease et al., *Pharmacognosy*, 11th Ed., p. 463 (1978).
Tyler et al. *Pharmacognosy*, 8th Ed., p. 148 (1981).
Vogel, *American Indian Medicine*, pp. 83, 399, 469–470 (1970).
Lust, *The Herb Book*, p. 407 (1974).
*The Merck Manual*, 15th Ed., pp. 1249–1250 (1987).
Lee, *Official Preparation of Pharmacy*, pp. 437–438 (1953).

*Primary Examiner*—Johnnie R. Brown
*Assistant Examiner*—Ralph Gitomer
*Attorney, Agent, or Firm*—Dianne E. Reed

[57] ABSTRACT

Methods and formulations are provided for alleviating the dryness of mucosal membranes in the upper and lower respiratory tract and gastrointestinal tract. The compositions are formulated into aerosol sprays and delayed release tablets which include eriodictyon fluid which is a Yerba Santa extract. The formulations may additionally contain other components such as preservatives, bronchodilators, choleretics, antibiotics, topical anesthetics, coloring agents, emulsifiers, and the like. The Yerba Santa-based compositions of the invention are administered to an affected patient to alleviate or prevent dryness on the mucosal membranes of the respiratory and gastrointestinal tracts.

19 Claims, No Drawings

ERIODICTYON COMPOSITIONS AND METHODS FOR TREATING INTERNAL MUCOUS MEMBRANES

CROSS-REFERENCE TO RELATED APPLICATION

This application is a continuation-in-part of pending U.S. application Ser. No. 07/499,952, filed Mar. 26, 1990, now U.S. Pat. No. 5,015,474 which application is a continuation-in-part of pending U.S. application Ser. No. 07/275,124, filed Nov. 22, 1988, now U.S. Pat. No. 4,938,963, to which applications I claim priority under 35 USC §120 and which applications are each incorporated herein by reference.

FIELD OF THE INVENTION

The invention relates generally to methods of treatment and to pharmaceutical compositions. More particularly, the invention relates to novel aerosol and oral pharmaceutical compositions for alleviating the dryness of mucosal membranes of the respiratory and gastrointestinal tracts, respectively. The active ingredient of the novel compositions include Yerba Santa fluid extract, which is eriodictyon fluid.

BACKGROUND OF THE INVENTION

All mammals, and in particular humans, can suffer from dryness on particular areas of the body. The skin and mucosal membranes of the body are most often affected. With respect to mucosal membranes, the dryness is the result of the generation of an insufficient quantity of mucoproteins and mucopolysaccharides on the affected area to hold fluid in contact with the cells. When insufficient moisture is present, the mucoproteins and mucopolysaccharides cannot create a sufficient barrier to irritation and infection. Accordingly, the affected individual is subjected to a higher degree of local infections with respect to the affected area, and such local infections can spread systemically. When such a systemic infection results, the consequences can be quite serious. Accordingly, it is important not only to relieve dryness in affected areas, but also to prevent the initial formation of dryness and therefore prevent the initial infections. Because the respiratory (upper and lower tracts) and gastrointestinal tracts are exposed to large amounts of foreign material, including bacteria and viruses, it is particularly important to maintain intact mucosal membranes in these areas.

A number of different compositions and methods for treating various types of dryness are described within the literature. For example, U.S. Pat. No. 4,232,003, issued Nov. 4, 1980, to Posthuma et al., discloses a composition referred to as a synthetic physiological mucous which is indicated as having particular usefulness in connection in treating the dryness of vaginal tissues and as a surgical lubricant. The composition is a pituitous aqueous solution of a high molecular polyacrylamide. Such synthetic mucous compositions and methods for using such compositions to treat dryness are also disclosed within U.S. Pat. No. 3,965,906, issued Jun. 29, 1976.

The general concept of imparting lubricicity to a substrate such as skin, hair or mucous membranes is discussed within U.S. Pat. No. 4,128,631, issued Dec. 5, 1978. The inventors disclosed the use of a composition which includes a high molecular weight salt having a particular structural formula and molecular weight range.

A more specific type of lubricating composition in the form of a vaginal suppository is disclosed within U.S. Pat. No. 4,347,237, issued Aug. 31, 1982. The suppository is solid at room temperature and melts at body temperature due to its composition which includes a variety of different types of water soluble polyoxy alkaline polyol components.

As indicated above, the literature includes a number of disclosures of compositions and methods of applying those compositions to a substrate such as skin or mucous membranes in order to improve lubrication or relieve dryness. The effect is generally obtained by the application of a synthetic lubricant or a synthetic moisturizer and not by the inclusion of an active ingredient within the composition. However, U.S. Pat. No. 4,184,974, issued Jan. 22, 1980, to Leuven, discloses a lubricant composition which includes a topical biocidal agent. A similar type of composition containing such a biocidal agent is disclosed within U.S. Pat. No. 4,267,168, issued May 12, 1981.

The present invention is premised on the surprising discovery that the oil extracted from the Yerba Santa plant (*Eriodictyon californicum; Eriodictyon glutinosum;* also known as "consumptive's weed"; "bear's weed" "mountain balm" and "gum plant") is extremely effective in providing long-lasting relief of a variety of types of mild to severe dryness of internal mucosal membranes (specifically in the respiratory and gastrointestinal tracts), with no unpleasant side effects.

The Yerba Santa plant is an evergreen shrub indigenous to the hills and mountains of California and northern Mexico, and was long used by Indians for a number of purposes. See, e.g., A. R. Hutchens, *Indian Herbalogy of North America,* Ontario: Merco, 1975, at pp. 317–318. A number of references to the Yerba Santa plant teach its use as an expectorant (e.g., N. Coon, *The Dictionary of Useful Plants,* Emmaus, Pa.: Rodale Press, (1974)), in treating colds, sore throats, catarrh, stomach aches, vomiting and diarrhea (see A. R. Hutchens, supra), in treating hemorrhoids (D. G. Spoerke, *Herbal Medications,* Santa Barbara, Calif.: Woodbridge Press, 1980, at p. 183), in treating diseases of the lung (*Los Remedios de la Gente: A Compilation of Traditional New Mexican Herbal Medicines and Their Use,* compiled by M. Moore, 1977), and in masking the taste of quinine and other bitter medications (Spoerke, supra; see also G. E. Trease et al., *Pharmacognosy,* London: Cassell & Colber, 1978, at p. 463)).

In a book entitled "The Herb Book", first edition, Benedict Lust Publications, New York, 1974, it is indicated that American Indians smoked or chewed the leaves as a cure for asthma. They also used the leaves as a tea for colds and for a mouthwash preparation. Drying and smoking the leaves as well as boiling the leaves in water is disclosed in other publications such as The Herb Book wherein it is indicated that Yerba Santa is an excellent expectorant, valuable for colds, chronic laryngitis, bronchitis, lung problems and asthma.

A book entitled "Herbal Medications", by David G. Spoerke, Jr., published by Woodridge Press Publishing Company, Santa Barbara, Calif., 1980, discloses what appears to be the main use of the Yerba Santa extract which is to combine the extract with other substances in order to mask the bitter taste of a substance such as quinine. On page 183, the book specifically indicates that "The volatile oil has irritant properties that make it useful as an expectorant." The book also indicates that "The volatile oil could be irritating to the mucous membranes of the gastrointestinal tract if a large amount were taken."

In the book "Pharmacognosy (Eleventh Edition)", published by Bailliére Tindall, London, 1978, the eriodictyon fluid is described under the section entitled "Volatile Oils and Resins" and is again indicated as being a vehicle used for masking the taste of bitter and otherwise disagreeable medicines, particularly quinine.

Publications discussing the Yerba Santa plant include the Coon, Hutchens, Moore, Spoerke, and Trease et al. references, cited in the preceding section, as well as V. J. Vogel, *American Indian Medicine*, The University of Oklahoma Press, 1970, at pp. 83, 399-400; W. H. Lewis et al., *Medical Botany: Plants Affecting Man's Health*, New York: John Wiley & Sons, 1977, at p. 301; P. Huson, *Mastering Herbalism: A Practical Guide*, New York: Stein and Day, 1974, at p. 32; B. C. Harris, *The Complete Herbal*. Barre, Mass.: Barre Publishers, 1972, at p. 197; N. Coon, *Using Plants for Healing*, Hearthside Press, 1963, at p. 122; M. Grieve, *A Modern Herbal*. vol. 22, New York: Hafner Publishing Co., 1959, at p. 865; and V. E. Tyler et al., *Pharmacognosy*, Philadelphia: Lee & Febiger, 1981, at p. 148.

There are known possessing what is referred to as mucolytic activity on both purulent mucous and non-purulent mucous. Perhaps the most well known is N-acetylcysteine.

Because N-acetylcysteine has some undesirable properties, attempts have been made to develop new compounds. One such group of compounds is disclosed by Maltz in U.S. Pat. No. 4,409,138, issued Oct. 11, 1983. This patent discloses compounds which have topical mucolytic activity in particular on secretions of the respiratory passages. The compound are indicated as being particularly desirable in that they are not absorbed by the tissues which they come into contact with, but are able to reach the gastrointestinal tract unaltered, where they are metabolized to non-toxic products which can be completely eliminated from the body without undesirable side effects. Similar compounds are disclosed by Maltz within U.S. Pat. No. 4,559,322 issued Dec. 17, 1985.

Other compounds have been disclosed which act as inhibitors of mucous secretion. Such compounds are disclosed within U.S. Pat. No. 4,939,169 issued Jul. 3, 1990 to Bundy et al.

Mucolytic compounds have been known for some time as exemplified by Canadian Patent 821,525 issued Aug. 26, 1969. This patent discloses N-acetylcysteine compositions which include a variety of excipient materials along with the active ingredient of N-acetylcysteine. A number of other active ingredients may be combined with the N-acetylcysteine in order to obtain a desirable pharmacological effect. Mention is made of using suitable aerosol propellants.

Other mucolytic compounds which are formulated within aerosol and oral dosage forms are disclosed with European Patent Application 0,015,544 published Sep. 17, 1990.

Based on the above publications, it appears as though there is a considerable art disclosing eriodictyon fluid and some possible pharmaceutical uses. There is also art disclosing mucolytic compounds which can be placed in the form of aerosols or oral formulations. However, the invention disclosed herein relates to specific eriodictyon fluid formulations which are applied to internal mucosal membranes in order to promote the formation of mucous on internal membranes. The pharmaceutical formulations and methods of using such are described in detail below.

SUMMARY OF THE INVENTION

The invention includes a method for alleviating dryness of the respiratory and gastrointestinal tracts comprising administering respectively an aerosol and a delayed-release composition of eriodictyon fluid extract to a patient. The compositions of the invention are pharmaceutical formulations which administered so as to coat the mucous membrane surfaces they are applied to.

It is an object of the invention to provide a method for treating various types of dryness of internal membranes in the respiratory and gastrointestinal tracts, comprising topically administering, to the surface of the tract of an affected individual, a formulation capable of coating an effective amount of eriodictyon fluid onto membrane so as to alleviate the symptoms of dryness.

It is another object of the invention to provide an aerosol composition for the upper and lower respiratory tracts and specifically for pulmonary administration which composition contains eriodictyon fluid, an aerosol propellant and a suitable excipient material which is pharmacologically compatible with the eriodictyon fluid and nonirritating to the pulmonary tract to which it is applied.

An important object of the invention is to provide aerosol formulations which include a combination of eriodictyon fluid with another active component such as a bronchial dilator or steroidal compound normally used in connection with the treatment of respiratory tract.

An important advantage of the aerosol formulations of the invention is that the eriodictyon fluid counters the drying effect normally experienced by users of aerosol formulations due to the presence of the low boiling point propellent as well as the drying effect which is often obtained by other active ingredients such as steroidal compounds and bronchial dilators.

An important feature of the invention is that the aerosol formulations provide for better absorption of active ingredients such as bronchial dilators and steroidal compounds.

It is yet another object of the invention to provide a composition in a delayed-release formulation which when administered orally will provide eriodictyon fluid to the membrane surface of the gastrointestinal tract.

It is a further object of the invention to provide such a method wherein the aerosol composition to be administered contains eriodictyon fluid, a bronchodilator and a preservative.

It is still a further object of the invention to provide a delayed-release Yerba Santa-based composition for treating various types of dryness of the gastrointestinal tract.

It is yet a further object of the invention to provide a composition for treating dryness which contains eriodictyon fluid and one or more excipients and additional components selected from the group consisting of steroidal compounds, bronchial dilators, antibiotics, antiulcer compounds, preservative, bactericide, antivirals, antidiuretics and anesthetics.

These and other object, advantages and features of the present methods and compositions for alleviating dryness will become apparent to those persons skilled in the art upon reading the details of the composition and usage as more fully set forth below, reference being made to the accompanying general and specific composition examples forming a part hereof.

DETAILED DESCRIPTION OF THE PREFERRED EMBODIMENTS OF THE INVENTION

Before the aerosol and delayed-release eriodictyon fluid-based formulations and methods for treating and preventing dryness are described, it is to be understood that this invention is not limited to the particular compositions or methods described as such compositions and methods may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a," "an" and "the" include plural referents unless the context clearly dictates otherwise. Thus, for example, reference to "an aerosol" includes mixtures of aerosols, reference to "an excipient" includes reference to mixtures of such excipients, reference to "the method" or "the step" includes a variety of such methods or steps of the type known to those skilled in the art, and so forth.

In its broadest sense, the invention encompasses a method of treating mucosal dryness on an internally located membrane by the administration of a topical composition of Yerba Santa fluid extract to an affected patient. By "Yerba Santa fluid extract" as used herein is meant the eriodictyon fluid which may be extracted from dried Yerba Santa leaves. One exemplary method for obtaining this Yerba Santa fluid extract is set forth in *Remington's Pharmaceutical Sciences*, 17th Ed., 1985, at pp. 1286 and 1516, which is incorporated herein by reference to disclose such an extraction method. As described in detail therein, the dried Yerba Santa plant is preferably processed in alcohol and water, followed by straining, pressing and clarification by, e.g., decantation or filtration.

In accordance with one embodiment, an aerosol formulation of eriodictyon fluid extract is administered to the upper and lower respiratory tracts by spraying and inhaling the formulation. The composition will preferably contain in the range of 0.25 wt. % to 10 wt. %, more preferably 0.5 wt. % to 5.0 wt. %, and most preferably about 1.25 wt. % eriodictyon fluid extract.

Depending on the area to which the composition is applied the composition will also contain one or more additional active ingredients such as antiasthma compounds, steroids, anti-inflammatory agents, bronchial dilator, antihistamines and antibiotics, in total comprising about 0.1 wt. % to 30 wt. %, more preferably 10 wt. % to 20 wt. %, with the amount varying with the class and specific type of ingredient used. Specific examples of compounds in each of these general classes are given in the *Physicians Disk Reference* which is incorporated herein by reference to disclose and describe such compounds. Additional therapeutic agents which might be combined with the eriodictyon fluid (in similar amounts to those indicated above) in an aerosol formulation include vasoconstrictors, vasodilators, sulfa drugs, enzymes, surfactants and antiseptics.

The eriodictyon fluid can be used in combination with a range of additional active ingredients. It must be kept in mind that the eriodictyon fluid is being administered in order to promote the formation of mucous on a internal membrane. Accordingly, the eriodictyon fluid should not generally be formulated with mucolytic compounds which break up mucous and/or compounds which inhibit mucous excretion. In addition to considering the pharmacological affect of any active ingredients combined with the eriodictyon fluid, those skilled in the art will make note of the physical characteristics of such active ingredients as taken alone, or in combination with eriodictyon fluid so as to chose ingredients which can be formulated into desirable formulations, such as sprays or aerosols which can be efficiently delivered to the respiratory tract.

Aerosol formulations have been used for sometime to treat various abnormalities of the respiratory tract. Aerosol formulations are effective in that they provide the active ingredient directly to the tissue which needs to be treated. However, many of the active ingredients which are brought into the contact with the respiratory tract can have a drying effect on the mucous membranes of the respiratory tract. Further, aerosol formulations are generally comprised of a large amount of a low boiling point hydrocarbon or low boiling point fluorocarbon which can dissolve and/or dry the mucous on the internal membranes of the respiratory tract. Therefore, although such formulations can be effective in obtaining a particular result such as bronchial dilation, the same formulations can have an undesirable drying effect on the mucous membranes. The present invention provides a means for counterbalancing the mucous drying or mucous dissolving effect caused by some active ingredients and/or propellants. By including the eriodictyon fluid with the propellants and/or other active ingredients, it is possible to remoisten the membranes and/or maintain the mucous membranes intact. The eriodictyon fluid can be formulated by itself with a propellant and administered after the administration of another compound or formulated together with another active ingredient so that both compositions can be applied simultaneously.

The precise dose of eriodictyon fluid to be administered in an aerosol formulation varies depending on a number of factors. Most importantly, the need for the eriodictyon fluid will vary depending on the need of the particular patient to prevent and/or alleviate dryness of the respiratory tract. Some patients have excess mucous and should not be prescribed eriodictyon fluid. Other patients suffer from severe loss of fluid on many surfaces and would require repeated administration of the aerosol formulation. Precise doses will depend on other factors such as the size and responsiveness of the patient. Dosing will generally be in similar amounts to the dosing of the other active ingredient such as the bronchial dilator being administered. Precise amounts will be determined by the care giver based on patient responsiveness.

In accordance with another embodiment of the invention a delayed release formulation of eriodictyon fluid extract is administered to the gastrointestinal tract. The delayed release of formulations of the invention include conventional delayed release formulations which incorporate the eriodictyon fluid extract therein. When the delayed release of formulations are administered orally the active ingredient (i.e., the eriodictyon fluid extract) is not released in the stomach due to the composition of the delayed release formulation. After the formulation moves into the intestines, release of the eriodictyon fluid begins. The fluid is thus administered along the intestines where it comes into contact with the internal surfaces of the intestine walls and thereby alleviates dryness and promotes the formation of mucosal membranes. A typical delayed release formulation includes about 10 to 200 mg. of eriodictyon fluid in a delayed release capsule, caplet or tablet. A typical dose involves the oral administration of one to four tablets. However, the specific amount of eriodictyon fluid administered and the frequency of the administration will be determined by the care giver depending on the size and condition of the patient and their responsiveness to the eriodictyon fluid.

Aerosol or delayed release formulations of the invention may also contain a preservative which is added to increase shelf life. Preferred preservative compounds include quaternary ammonium bacteriostases such as benzalkonium chloride, present in an amount ranging from about 0.25 wt. % to about 5.0 wt. %, preferably about 0.5 wt. %. Incorporation of any of phenyl mercuric acetate, thimerosal, or benzyl alcohol into the present composition also serves to retard bacterial growth in the composition.

Specific examples of aerosol and delayed release formulation ingredients and preferred formulation amounts will be exemplified hereinbelow.

In order to provide for a uniform distribution of active ingredient in a formulation it may be desirable to include a dissolution-assisting agent. Examples of such agents include non-ionic surface active agents, such as polyoxyethylenesorbitan monooleate, polyoxyethyleneoxystearic acid triglyceride, polyethylene glycol, etc.

The formulations of the invention may include a pH buffer. The pH of the aerosol formulations of this invention is preferred to be 6.5-8.5, particularly about 7.5.

A particularly preferred embodiment of the invention is a pressurized aerosol formulation composition in a form suitable for pulmonary administration carried out by simultaneously spraying and inhaling. In such a composition the eriodictyon fluid is present in a low boiling point carrier and perhaps water.

Detailed information regarding the formulation of aerosols is present within *Remington's Pharmaceutical Sciences*, 17th Edition, Mack Publishing Company, 1985, Chapter 93, pp. 1662-1677 which is incorporated herein by reference to disclose information regarding the aerosol formulations which can be used in connection with the present invention to provide aerosols containing eriodictyon fluid. Although a number of aerosol systems are possible, the simplest provides a solution or suspension of active ingredients in a liquid propellant such as a low boiling point compound such as a short (1–4C) chain hydrocarbon or fluorinated hydrocarbon or a mixture of such propellants in combination with a solvent. In such a system, both the liquid and vapor phases are present. When the valve on a container of such a formulation is depressed, liquid propellant containing dissolved acted ingredients and other solvents is released. Depending upon the nature of the propellants used, the quantity of propellant present and the valve mechanism, a fine mist or wet spray is produced due to the large expansion of the propellant at room temperature and atmospheric pressure. Such a system can be used to formulate aerosols for inhalation through the mouth into the respiratory tract or nasal application into the respiratory tract.

A variety of fluorocarbon propellants are used although dichlorofluoromethane and dichlorotetrafluoroethane are commonly used in oral aerosols. In addition to fluorocarbon propellants, various low boiling point hydrocarbon propellants or compressed gases may be used to provide aerosol formulations. Some typical hydrocarbon propellants include propane, isobutane and n-butane. In addition, ethers can be used such as dimethylether.

It is pointed out that the present invention is attempting to obtain a coating on an internal mucosal membrane in the respiratory tract, particularly pulmonary tissues. Since it is desirable to coat the membrane and not have the eriodictyon fluid within the spray absorbed into the membrane, it is desirable to provide a relatively wet or coarse spray. This can be achieved by decreasing the amount of the low-boiling propellants and increasing the ratio of the eriodictyon fluid and/or solvents (e.g., water) which might be used in combination with this fluid. The eriodictyon fluid may be present in an amount in the range of about 20-75% with the propellant being present in an amount in the range of about 25-80%. With such formulations, particles produced generally range in the size of from 50 $\mu$m to 200 $\mu$m.

Such a liquid aerosol composition is generally comprised of about 20-99% (by weight) low boiling point propellant and about 1-80% (by weight) of the eriodictyon fluid of the invention. After providing for the essential components of the propellant and eriodictyon fluid, the pH of the composition is adjusted by adding pH buffers of the type generally known to those skilled in the art. The aerosol formulations of the invention are administered by spraying the formulation into the mouth and/or nose and inhaling at the same time. Accordingly, the sprayed formulations enter the bronchial passages and eventually the lungs. It is preferred to adjust the saline content of the aerosol formulation so as to closely match the bronchial and pulmonary environment to which the formulation is applied. This can be done by adding aqueous saline solutions of the type generally known to those skilled in the art. Adjustments in saline content and pH are preferably carried out so as to match as closely as possible the environment which the formulation is being applied to so as to reduce as much as possible any irritation which might be created by the formulations.

The aerosol formulation preferably includes a preservative such as sodium benzoate, which is generally present in relatively small amounts such as in the range of 0.1 wt. % to about 1 wt. %, more preferably about 0.25 wt. %.

The eriodictyon fluid component coats and protects an area and allows for the release of natural moisture from any substrate it is applied to such as mucous membrane substrates in the respiratory and gastrointestinal tracts.

The excipient materials for aerosol formulations of the invention may include pigments, fillers, extenders, preservatives, and antioxidants can also be included in the composition, but it is ordinarily preferred to avoid the use of any filler, extender, or pigment which will leave a visible solid residue. For antioxidant or preservative effects, various FDA-approved compounds are suitable, including the conventional alkylated hydroxy aromatic compounds such as BHT (butylated hydroxytoluene) or BHA (butylated hydroxyanisole).

In general, it is not necessary to particularly adjust the pH of the delayed release formulation. What is necessary is that the formulation be adjusted so that it is responsive to the pH as it is exposed to and that its responsiveness obtains the objects of the invention.

EXAMPLES

The following examples are provided so as to provide those of ordinary skill in the art with a complete disclosure and description of how to make the formulations and methods of the invention and are not intended to limit the scope of what the inventors regard as their invention. Efforts have been made to insure accuracy with respect to numbers used (e.g., amounts, temperature, etc.) but some experimental errors and deviation should be accounted for. Unless indicated otherwise, parts are parts by weight, temperature is in degrees C, and pressure is at or near atmospheric.

EXAMPLE 1

| Ingredients | Quantity |
| --- | --- |
| Excipient (carrier) | 1.0–99.0 wt. % |
| Yerba Santa Fluid Extract* | 99–1.0 wt. % |
| Other Components | 0–9.0 wt. % |

*Dried eriodictyon can be obtained from Meer Corporation, North Bergen, New Jersey. It can be used to prepare the fluid extract in a manner substantially as described in Remington's Pharmaceutical Sciences, 17th Ed., cited supra, on pages 1286 and 1516. After preparation of the fluid extract, the above ingredients can be mixed to give a formulation of Yerba Santa fluid extract.

EXAMPLE 2

| Ingredients | Quantity |
| --- | --- |
| Water/Aerosol Propellant | 80.00 wt. % |
| Yerba Santa Fluid Extract* | 19.75 wt. % |
| Preservative | 0.25 wt. % |

One to two sprays of one second duration of the above aerosol composition can be administered as needed to obtain relief from or prevent dryness of the pulmonary tract.

EXAMPLE 3

| Ingredients | Quantity |
| --- | --- |
| Excipient (fluorocarbon/solvent) | 20–30 wt. % |
| Yerba Santa Fluid Extract* | 80–70 wt. % |

The excipient also preferably includes a preservative such as sodium benzoate in an amount of about 0.1 to 0.5 wt. %. The formulation can be formed into a tablet or capsule and administered orally.

EXAMPLE 4

| Ingredients | Quantity |
| --- | --- |
| Aerosol Propellant/Water | 20 wt. % |
| Yerba Santa Fluid Extract* | 79.75 wt. % |
| Sodium Benzoate | 0.25 wt. % |

This composition is in the form of an aerosol which can be applied to the respiratory tract so that they reach deep internal areas of the pulmonary tract.

EXAMPLE 5

| Ingredients | Quantity |
| --- | --- |
| Polystyrene Polymer | 98.75 wt. % |
| Yerba Santa Fluid Extract* | 1.00 wt. % |
| Sodium Benzoate | 0.25 wt. % |

This composition is a solid tablet for delay release in the intestines after oral administration.

EXAMPLE 6

| Ingredients | Quantity |
| --- | --- |
| Fluorocarbon Propellant/Water | 96.75 wt. % |
| Yerba Santa Fluid Extract* | 1.00 wt. % |
| Sodium Benzoate | 0.25 wt. % |
| Bronchial Dilator | 2.0 wt. % |

EXAMPLE 7

| Ingredients | Quantity |
| --- | --- |
| n-Butane/Water | 95.75 wt. % |
| Yerba Santa Fluid Extract* | 3.00 wt. % |
| Sodium Benzoate | 0.25 wt. % |
| Theophylline | 1.0 wt. % |

EXAMPLE 8

| Ingredients | Quantity |
| --- | --- |
| Propane/Water | 97.50 wt. % |
| Yerba Santa Fluid Extract* | 1.25 wt. % |
| Sodium Benzoate | 0.25 wt. % |
| Antibiotic | 1.0 wt. % |

EXAMPLE 9

| Ingredients | Quantity |
| --- | --- |
| Polypropylene | 50.0–99.0 wt. % |
| Yerba Santa Fluid Extract* | 1.0–50.0 wt. % |
| Preservative | 0.25 wt. % |

EXAMPLE 10

| Ingredients | Quantity |
| --- | --- |
| Polystyrene | 40.0 wt. % |
| Polypropylene | 47.5 wt. % |
| Yerba Santa Fluid Extract* | 11.25 wt. % |
| Sodium Benzoate | 0.25 wt. % |
| Choleretic Agent | 1.0 wt. % |

EXAMPLE 11

| Ingredients | Quantity |
| --- | --- |
| Dimethylether/Water | 20% wt. % |
| Eriodictyon Fluid | 79% wt. % |
| Steroidal | 1.0 wt. % |

The above general example could, of course, include preservatives. The pH of the composition is adjusted to match the pH of the mucosal tissues of the respiratory tract the composition is applied.

More particularly, the delayed release formulation is administered orally and comes into contact with the extremely low pH of the stomach. At this point (in the stomach), the formulation should not be dissolved so as to release the eriodictyon fluid contained therein. It is desirable if none of the eriodictyon fluid is released within the stomach and that essentially all of the eriodictyon fluid remains within the formulation intact until the formulation passes out of the stomach. When material passes out of the stomach into the intestines, it comes into contact with an alkaline pH environment. Accordingly, the delayed release formulation should be formulated so that after exposure to acid, it becomes broken down when it is exposed to alkaline excretions within the intestines. Preferably, the release of the eriodictyon fluid in the intestines is somewhat gradual so that the eriodictyon fluid is spread over a substantial portion of the intestines and is therefore allowed to coat a substantial portion of the mucous membranes substrates lining within the intestines. Those skilled in the art are capable of formulating delayed release formulations so as to obtain these objects.

Small amounts of a variety of different biocidal agents can be included in the formulations of the invention. They may be added to kill bacteria or virus or both on the substrate. Further, they may be added to prevent or hinder bacterial growth in the formulation during storage. The inclusion of silver ions are known to have such an effect and can be included in amounts of 10 to 500 ppm by adding silver nitrate to the composition. Such biocidals are described in U.S. Pat. No. 4,267,168, issued May 12, 1981.

It is preferred that the composition contain one or more preservatives, typically an antioxidant present in an amount effective to retard oxidation and/or inactivation of the fluid extract. As with other additives, both active and inactive, the selection will be readily made by one skilled in the art. Examples of suitable preservatives include ascorbyl palmitate, butylated hydroxyanisole, butylated hydroxytoluene, potassium or sodium sorbate, sodium bisulfite, sodium metabisulfite, sorbic acid, sulfur dioxide, and sodium or potassium benzoate. A particularly preferred preservative for use in formulations of the invention is sodium benzoate.

Other components which may, if desired, be incorporated into the present composition include coloring agents, which may be either natural or synthetic, diluting agents, emulsifying agents, excipients, pH buffering agents, and the like.

Suitable colorants include dyes that are generally suitable for food, drug and cosmetic applications, i.e., those known as "F.D. & C." dyes. Where the Yerba Santa composition is in an aerosol form, acceptable dyes should be soluble in the propellant. Illustrative examples include the disodium salt of 5,5-indigotin-disulfonic acid ("F.D. & C. Blue No. 2") and the monosodium salt of 4-[4-N-ethyl-p-sulfobenzylamino)-diphenylmethylene]-[1-(N-ethyl-N-p-sulfonium-benzyl)-2,5-cyclohexadienimine ("F.D. & C. Green No. 1"). Reference may be had to the Kirk-Othmer Encyclopedia of Chemical Technology, 3rd Ed., in Volume 6, for further F.D.& C. colorants and corresponding chemical structures.

In order to provide for the administration of the eriodictyon fluid to the mucosal membranes of the intestines, it is necessary to formulate the fluid into a delayed release formulation. A variety of sustained-release/-delayed release drug delivery systems are disclosed with the above-cited *Remington's Pharmaceutical Sciences* publication at Chapter 92, beginning at page 1644 which information is incorporated herein by reference specifically to disclose delayed release formulations which can be formulated with eriodictyon fluid to provide formulations of the present invention.

Delayed release formulations of the invention can be in the form of tablets, capsules, caplets and other variations as discussed within Remington's and which will be known to those of ordinary skill in the art of providing for delayed release oral formulations. In connection with the present invention, it is desirable to formulate the eriodictyon fluid into an oral formulation such as tablets, capsules and microcapsules which will pass through the stomach and upper intestines before they begin deterioration. Once in the lower intestines, deterioration of the polymer coating begins allowing for a release of the eriodictyon fluid contained therein. Preferably, the deterioration of the polymers in the formulation occurs at different times so that the eriodictyon fluid can be released over the entire length or a relatively substantial length of the lower intestines and thus provide the eriodictyon fluid to a large surface area, i.e., a major proportion of the surface area of the lower intestines.

The delayed release formulations of the invention may include the eriodictyon fluid formulated by itself (with the appropriate excipients) to allow for the delayed release results desired. However, formulations of the invention may include other active ingredients such as choleretics, e.g., alibendol, dehydrocholic acid, hymecromone, piprozolin, sincalide and tocamphyl. These pharmaceuticals may be administered to patients suffering from various forms of intestinal abnormalities. Other similar pharmaceuticals will be known to those skilled in the art and are disclosed and described within the above-cited *Physicians Desk Reference*.

The delayed release formulations may include excipient materials such as a number of substances of synthetic origin including styrene and butadiene-styrene polymers, isobutyleneisoprene copolymers, paraffin, petroleum wax, polyethylene, polyisobutylene, polyvinylacetate, etc., plasticizers or softeners such as lanolin, stearic acid, sodium stearate, potassium stearate, glycerol triacetate, glycerine, etc.

Waxes, including low melting point natural and synthetic waxes, petroleum waxes, paraffin waxes and microcrystalline waxes may also be incorporated into the delayed release formulation.

The amount of Yerba Santa extract administered will, of course, be dependent on the subject being treated, the severity of the dryness, and the judgment of the prescribing health care professional. However, an effective dosage regimen will typically be 1-2 sprays of aerosol of one second duration containing 0.25 wt. % to 10 wt. % Yerba Santa fluid extract. It is preferred that a sufficient dose be provided so that the extract be retained in contact with the mucous membrane being treated for a time sufficient to allow the Yerba Santa fluid extract to fully coat and remain on the membrane for a substantial period of time. The coating should remain in place for sufficient time to allow the natural membrane to replace itself. Reapplication of a formulation of the invention to the dry area may be and often is required in order to obtain the desired results.

EXAMPLE 12

| Ingredients | Quantity |
| --- | --- |
| Water/propellant | 20-80 wt. % |
| Eriodictyon Fluid | 80-20 wt. % |
| pH Buffer | 0.0-9.0 wt. % |
| Sodium Chloride | 0.01-5.0 wt. % |

The above composition may further include other active components such as decongestants. The sodium chloride is added in an amount to adjust to the saline composition of normal respiratory tract mucosal tissues, as is the pH of the composition.

While the present invention has been described with reference to the specific embodiments including methods and formulations for treating dryness, it should be understood by those skilled in the art that various changes may be made and equivalents may be substituted without departing from the true spirit and scope of the invention. In addition, many modifications may be made to adapt a particular substrate surface to be treated, excipient, material, composition of matter, process, process step or steps, to the objective, spirit and scope of the present invention. All such modifications are intended to be within the scope of the claims appended hereto.

I claim:

1. A method of imparting moisture to the pulmonary tissue of an individual in need of such treatment, comprising administering to said individual a pressurized aerosol formulation suitable for pulmonary administration, wherein the formulation comprises, in a low-boiling point hydrocarbon or fluorocarbon propellant, eriodictyon fluid extract in an amount sufficient to achieve an acceptable degree of moisture on the pulmonary tissue of the individual.

2. The method of claim 1, wherein the aerosol formulation contains approximately 1 to 80 wt. % eriodictyon fluid extract.

3. The method of claim 2, wherein the aerosol formulation contains approximately 0.25 to 10 wt. % eriodictyon fluid extract.

4. The method of claim 1, wherein the aerosol formulation additionally includes a preservative effective to retard oxidation of the formulation and retard bacterial growth therein.

5. The method of claim 4, wherein the preservative is selected from the group consisting of quaternary ammonium bacteriostases and sodium benzoate.

6. The method of claim 1, wherein the aerosol formulation additionally contains a pH buffer to maintain the pH of the formulation in the range of about 6.5 to 8.5.

7. The method of claim 1, wherein said administering is effected by spraying the formulation into the mouth of the individual.

8. The method of claim 1, wherein said administering is effected by spraying the formulation into the nose of the individual.

9. The method of claim 1, wherein said aerosol formulation comprises an additional pharmaceutically active component.

10. The method of claim 9, wherein said aerosol formulation further comprises a dissolution-assisting agent.

11. The method of claim 9, wherein the pharmaceutically active component is a bronchial dilator.

12. The method of claim 9, wherein the pharmaceutically active component is a steroid.

13. A method of imparting moisture to the pulmonary tissue of an individual in need of such treatment, comprising administering to said individual, by spraying into the mouth or nose, a pressurized aerosol formulation suitable for pulmonary administration, wherein the formulation comprises, in a low-boiling point hydrocarbon or fluorocarbon propellant, approximately 1 to 80 wt. % eriodictyon fluid extract, a preservative selected from the group consisting of quaternary ammonium bacteriostases and sodium benzoate, and a pH buffer to maintain the pH of the formulation in the range of about 6.5 to 8.5.

14. A pressurized aerosol formulation for imparting moisture to the pulmonary tissue of an individual in need of such treatment, comprising approximately 1 to 80 wt. % eriodictyon fluid extract, 20 wt. % to 99 wt. % low-boiling point hydrocarbon or fluorocarbon propellant, 0.25 wt. % to about 5 wt. % preservative, a pH buffer in an amount sufficient to provide the composition with a pH in the range of about 6.5 to about 8.5, and saline solution in an amount so as to match the saline content of tissues of the respiratory tract.

15. A method for imparting moisture to mucosal membrane substrates in the gastrointestinal tract of an individual in need of such treatment, comprising orally administering to the individual a delayed release formulation comprising eriodictyon fluid extract in an amount sufficient to achieve an acceptable degree of moisture on said mucosal membrane substrates, coated with a polymeric excipient material which is stable in an alkaline pH environment but bioerodes when exposed to an acidic pH, such that release of the eriodictyon fluid extract is prevented until the composition has reached the intestines of the individual.

16. The method of claim 15, wherein the delayed release formulation further includes a pharmaceutically acceptable choleretic compound present in sufficient amount so as to treat the gastrointestinal tract.

17. The method of claim 16, wherein the delayed release formulation comprises an additional pharmaceutically active component.

18. A delayed release formulation for imparting moisture to mucosal membrane substrates in the gastrointestinal tract of an individual in need of such treatment, comprising, in a unit dosage form, approximately 10 mg to 200 mg eriodictyon fluid extract and about 0.25 wt. % to about 5 wt. % preservative coated with a polymeric excipient material which is stable in an alkaline pH environment but bioerodes when exposed to an acidic pH, such that release of the eriodictyon fluid extract is prevented until the composition has reached the intestines of the individual.

19. The delayed release formulation of claim 18, further including a dissolution-assisting agent.

* * * * *